(12) United States Patent
Zhang

(10) Patent No.: US 8,092,217 B2
(45) Date of Patent: Jan. 10, 2012

(54) SUCKBACK PREVENTION DEVICE FOR SINGLE USE HIGH-SPEED TURBINE DENTAL DRILL HANDPIECE

(75) Inventor: Fudong Zhang, Beijing (CN)

(73) Assignee: Beijing North Pole Dental Handpieces Co., Ltd., Beijing (CN)

( * ) Notice: Subject to any disclaimer, the term of this patent is extended or adjusted under 35 U.S.C. 154(b) by 624 days.

(21) Appl. No.: 12/208,480

(22) Filed: Sep. 11, 2008

(65) Prior Publication Data

US 2009/0004623 A1    Jan. 1, 2009

Related U.S. Application Data

(63) Continuation of application No. PCT/CN2007/070113, filed on Jun. 14, 2007.

(30) Foreign Application Priority Data

Jul. 25, 2006    (CN) .......................... 2006 1 0200741

(51) Int. Cl.
*A61C 1/05* (2006.01)
*A61C 1/16* (2006.01)
(52) U.S. Cl. .................. 433/115; 433/116; 433/132
(58) Field of Classification Search .......... 433/114–116, 433/131–133; 606/79–85, 127–128, 167–189; 277/630, 634, 637, 585, 576; 408/124–137; 409/231–232, 175–182, 144, 230
See application file for complete search history.

(56) References Cited

U.S. PATENT DOCUMENTS

| 2,791,835 | A | * | 5/1957 | Staunt | 433/128 |
| 3,324,552 | A | * | 6/1967 | Saffir | 433/82 |
| 4,913,447 | A | * | 4/1990 | Jostlein | 277/304 |
| 5,779,474 | A | * | 7/1998 | Gonser | 433/129 |
| 7,048,540 | B2 | * | 5/2006 | Jikuhara et al. | 433/132 |
| 2009/0004623 | A1 | * | 1/2009 | Zhang | 433/132 |

FOREIGN PATENT DOCUMENTS

CN    2510028    *    9/2002

* cited by examiner

*Primary Examiner* — Todd Manahan
*Assistant Examiner* — Matthew Nelson
(74) *Attorney, Agent, or Firm* — Matthias Scholl P.C.; Matthias Scholl

(57) ABSTRACT

A high-speed turbine dental drill handpiece has a drilling needle, a wind wheel axle, a head housing having an annular opening with a two-step profile shape, and a suckback prevention device. The suckback prevention device includes an elastic bowl-shaped axle shroud coupled to an annular skeleton that are buckled in an inner step of the head housing and an annular screw connected to the outer step of the head housing (or retaining of the elastic bowl-shaped axle shroud. An eyelet for the drilling needle is set at the center of the elastic bowl-shaped axle shroud, the diameter of the eyelet being slightly larger than that of the drilling needle.

8 Claims, 3 Drawing Sheets

12# SUCKBACK PREVENTION DEVICE FOR SINGLE USE HIGH-SPEED TURBINE DENTAL DRILL HANDPIECE

CROSS-REFERENCE TO RELATED APPLICATIONS

This is a National Stage Application of International Patent Application No. PCT/CN2007/070113, with an international filing date of Jun. 14, 2007, which is based on Chinese Patent Application No. 200610200741.X, filed Jul. 25, 2006. The contents of these specifications including any intervening amendments thereto are incorporated herein by reference.

BACKGROUND OF THE INVENTION

1. Field of the Invention

The invention relates to the fields of medical instruments, and more particularly, to a hand-held dental instrument for drilling teeth.

2. Background of the Invention

High-speed turbine dental drill handpiece is an instrument for drilling teeth. It is inserted into the oral cavity of a patient and touches parts in the oral cavity such as teeth, oral mucosa, etc. As shown in FIG. 1, an existing high-speed turbine dental drill handpiece comprises a head 4, a drilling needle 3, a button cap 9, a front handle 1, and a back handle 2. The front handle 1 and the back handle 2 are held by hand during application. The rear portion of the back handle 2 is connected with a quick disconnect adapter. The quick disconnect adapter is connected to water and air lines of the dental unit. The supplied compressed air provides rotation power for the handpiece, and the supplied pressure water serves to cool the cutting position. When the drilling needle 3 is drilling teeth at a high-speed, it must be cooled with water. When drilling teeth, water saliva, and drilling sludge form contamination fluid. If the patient carries some transmissible disease such as hepatitis, AIDS, etc., the contamination fluid may contain dangerous pathogens. It is well known that a fluid suckback phenomenon will occur when the existing high-speed dental drill handpiece is drilling teeth. As shown in FIG. 2, when the powered wind wheel 7 is rotating, air for cooling the bearing flows out from the clearance space 17 between the bearing 6, the wind wheel axle 15, and the head housing 4. At this point, the air pressure inside of the head housing is higher than the atmospheric pressure, thus no suckback phenomenon occurs. However, when the drilling needle stops rotating, the powered wind wheel will still rotate for a certain time due to rotatory inertia. Since no compressed air to the air supply orifice 12 is supplied at that time, air is supplemented from the core portion of the wind wheel and flows into the head housing, and then discharges from the exhaust outlet of the head housing into the inner cavity of the handpiece handle and the behind exhaust passage, as shown in FIG. 3. At this time, if the contaminated fluid touches the front part of the head, the contaminated fluid will flow into the head housing 18, which is termed fluid suckback phenomenon. When the handpiece starts to operate again, the contaminated fluid sucked in the head will be pushed out from the head housing. This phenomenon will be repeated each time the drill stops and starts rotating. The contaminated fluid contaminates not only the handpiece, but also the adapter and pipelines. When using the same handpiece with another patient, the contaminated fluid will spray into the oral cavity of the patient, resulting in an iatrogenic cross infection.

SUMMARY OF THE INVENTION

Therefore, it is one objective of the invention to provide a suckback prevention device for a single use high-speed turbine dental drill handpiece to overcome the iatrogenic cross infection associated with contaminated fluid suckback phenomenon of the existing high-speed turbine dental drill handpiece.

In order to realize the above objective, provided is a suckback prevention device for single use high-speed turbine dental drill handpiece. The device is installed at the side assembled with the drilling needle of the head housing of the high-speed turbine dental drill handpiece which comprises a head, a drilling needle, a front handle, and a back handle. A powered wind wheel and a wind wheel axle driving the rotation of the drilling needle are installed in the clearance space between the head housing and the head cover, the wind wheel axle is supported by the bearing. An O-shaped vibration reduction ring is disposed between the bearing and the head housing, the upper end of the wind wheel axle is connected orderly to the button cap spring and the button cap. A water passage, an air passage, and a driving wind wheel air passage are set at the neck portion of the head, the compressed air inlet of the driving wind wheel is located in the powered wind wheel, wherein the lower end of the wind wheel axle is hidden inside of the head housing and is connected with the drilling needle, the edge of the head housing relative to the wind wheel axle and the drilling needle is an annular opening in a two-step profile shape; an elastic bowl-shaped axle shroud is buckled in the inner step of the head housing; an eyelet for the drilling needle is set at the center of the axle shroud; the size of the eyelet is slightly larger than the outer diameter of the drilling needle; an annular screw is screwed connected to the outer step of the head housing.

In a class of this embodiment or in another embodiment, the center portion of the axle shroud is relatively thick, while the annular strip between the center portion and the edge portion of the axle shroud is relatively thin.

In another class of this embodiment or in another embodiment, the axle shroud is embedded inside of an annular skeleton, the edge of the axle shroud and the annular skeleton are hot pressed together.

In another class of this embodiment or in another embodiment, the material for the axle shroud is rubber plastic or rubber polymer.

In another class of this embodiment or in another embodiment, the material for the annular skeleton is metal or hard plastic.

As a result, since an elastic axle shroud is installed between the wind wheel axle and the head housing, and is positioned by means of annular screw, the whole device is economy, is convenient to install, is safe and reliable to operate, is easy to assemble, and is suitable for single use high-speed dental drill handpiece. When the drilling needle is rotating operating, the axle shroud is blew out by the air flow of the head, then the end face of the axle shroud is separated with the end face of the wind wheel axle so that the rotation operation is not influenced. When in a free resting state, the axle shroud is light contacted the end face of the wind wheel axle to form axle shroud brake end face, then the back air flow is blocked outside of the head housing so that the contaminated fluid is prevented from flowing back into the dental drill handpiece, and thus, the iatrogenic cross infection is avoided effectively.

BRIEF DESCRIPTION OF THE DRAWINGS

The invention is described hereinbelow with reference to accompanying drawings, in which.

The reference numbers of the various parts shown in above drawings are listed below, in which front handle corresponds to the number 1; back handle—2; drilling needle—3; head housing—4; O-shaped vibration reduction ring—5; bearing—6; powered wind wheel—7; head cover—8; button cap—9; button cap spring—10; compressed air inlet of driving wind wheel—11; air passage of driving wind wheel—12; annular screw—13; axle shroud—14; wind wheel axle—15; axle shroud brake end face—16; air flow for cooling bearing—17; suckback air flow—18; water passage—19; air passage—20; compressed air—21; and annular skeleton—22.

BEST MODE OF CARRYING OUT THE INVENTION

Figure 1:
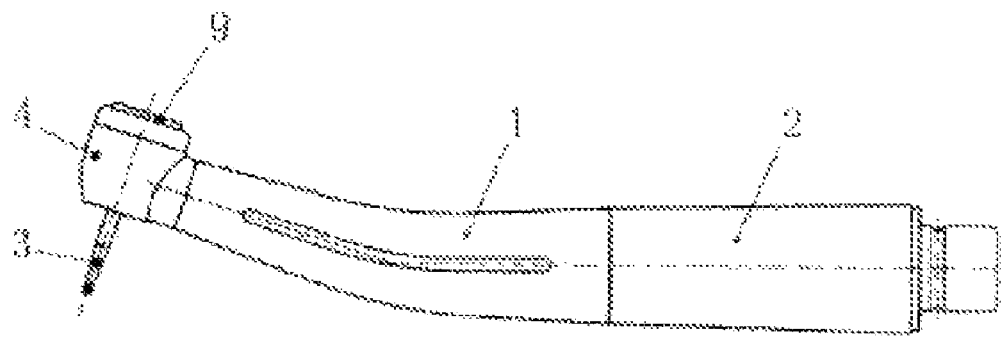
FIG. 1 illustrates a structural view of a single use suckback prevention high-speed turbine dental drill handpiece in accordance with one embodiment of the invention.
Figure 2:
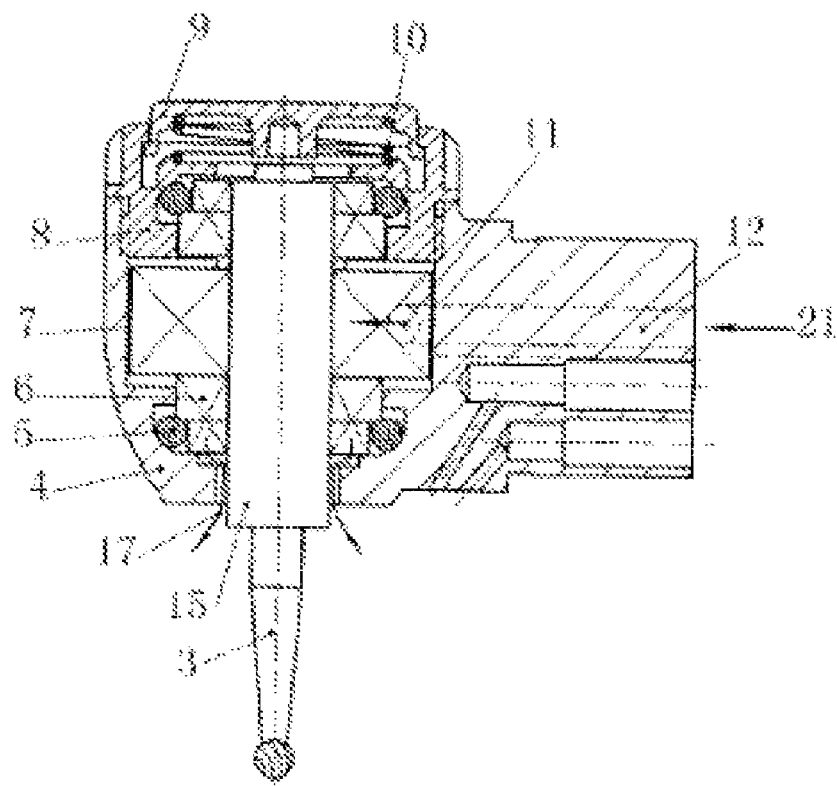
FIG. 2 illustrates a sectional view of the head housing of an existing high-speed turbine dental drill handpiece when the drilling needle is in rotational state.
Figure 3:
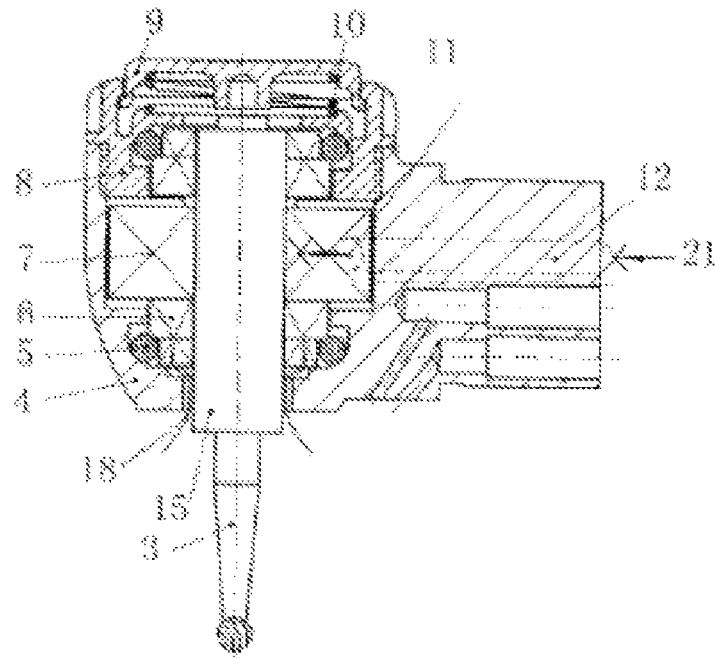
FIG. 3 illustrates a sectional view of the head housing of an existing high-speed turbine dental drill handpiece when the powered wind wheel is in inertia rotation state causing fluid suckback phenomenon.

With reference to FIG. 1, a suckback prevention device for single use high-speed turbine dental drill handpiece comprises a head housing 4, a drilling needle 3, a front handle 1, and a back handle 2. The suckback prevention device of the invention is installed at the end face of the drilling needle protruded out of the head housing for housing the wind wheel axle of the high-speed turbine dental drill handpiece.

Figure 4:
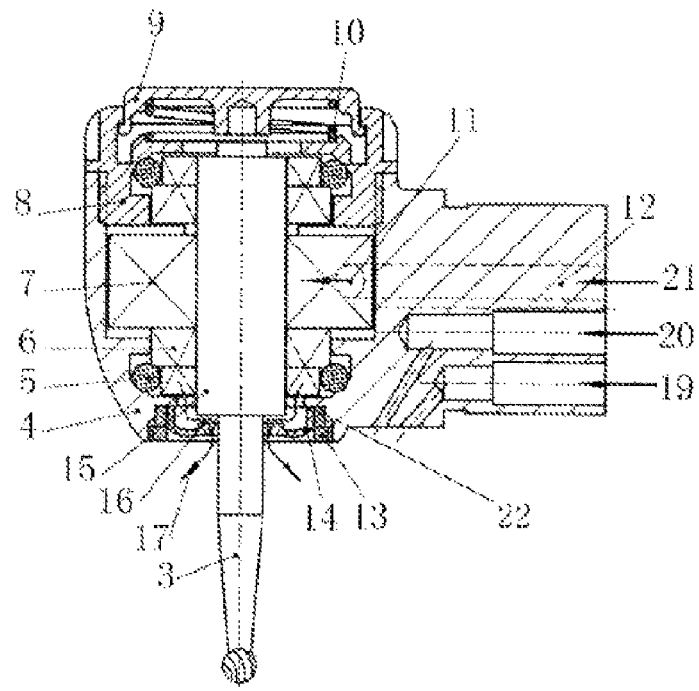
FIG. 4 illustrates a sectional view of the head housing of a single use suckback prevention high-speed turbine dental drill handpiece when the drilling needle is in rotation state in accordance with one embodiment of the invention.
Figure 5:
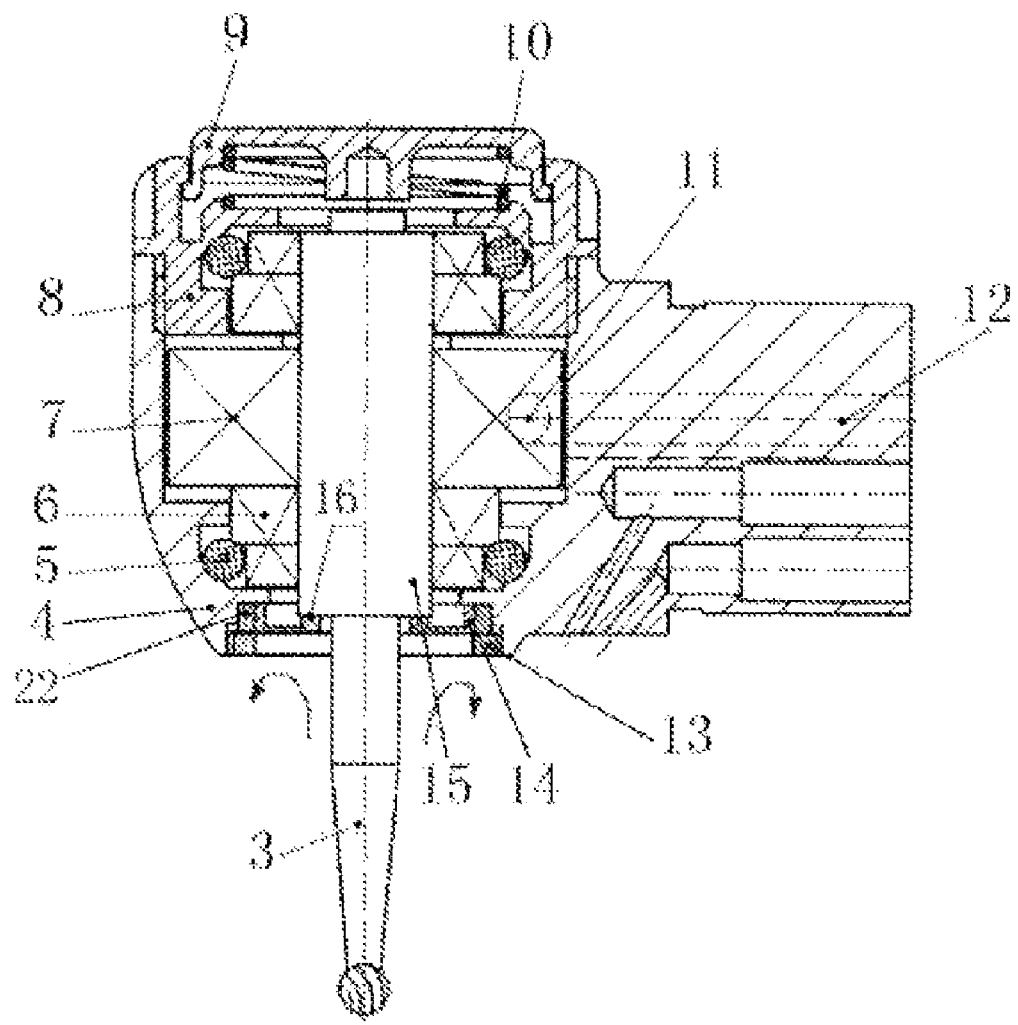
FIG. 5 illustrates a sectional view of the head housing of a single use suckback prevention high-speed turbine dental drill handpiece when the fluid suckback is blocked in accordance with one embodiment of the invention.

With reference to FIGS. 4-5, the powered wind wheel 7 and the wind wheel axle 15 driving the rotation of the drilling needle 3 are installed in the clearance space between the head housing 4 and the head cover 8, the wind wheel axle 15 is supported by the bearing 6; an O-shaped vibration reduction ring 5 is disposed between the bearing and the head housing; the upper end of the wind wheel axle 15 is connected orderly to the button cap spring 10 and the button cap 9; a water passage 19, an air passage 20, and a driving wind wheel air passage 12 are set at the neck portion of the head; the compressed air inlet 11 of the driving wind wheel is located in the powered wind wheel 7.

The lower end of the wind wheel axle 15 is hidden inside of the head housing 4 and is connected with the drilling needle 3, the edge of the head housing relative to the wind wheel axle and the drilling needle is an annular opening in a two-step profile shape; an elastic bowl-shaped axle shroud 14 is buckled in the inner step of the head housing; an eyelet for the drilling needle is set at the center of the axle shroud, and the size of the eyelet is slightly larger than the outer diameter of the drilling needle; an annular screw 13 is screwed connected to the outer step of the head housing.

The center portion of the axle shroud 14 is relatively thick, while the annular strip between the center portion and the edge of the axle shroud is relatively thin. The axle shroud 14 is embedded inside of an annular skeleton 22, the edge of the axle shroud and the annular skeleton are hot pressed together. The material for the annular skeleton is metal or hard plastic, while that for the axle shroud is rubber plastic or rubber polymer.

When in a free resting state, the inner surface of the axle shroud is light contacted the end face of the wind wheel axle 15. The axle shroud is fixed on the head housing 4 via means of a special annular screw 13. The drilling needle 3 is protruded out by passing though the center hole of the axle shroud 14, and the size of the center hole of the axle shroud 14 is slightly larger than the outer diameter of the drilling needle 3. The axle shroud is made of rubber plastic material and thus has a certain degree of elasticity and abrasion resistance capability.

FIG. 4 shows an operation status of the device of the invention, the axle shroud 14 is blown out by the air flow so that the inner surface of the axle shroud is separated with the end face of the wind wheel axle, then the air flow 17 for cooling the bearing flows out from the clearance space.

FIG. 5 shows an idle or brake status of the device of the invention, at this point the center portion of the axle shroud is contacted the end face of the wind wheel axle 15 to form axle shroud brake end face 16, so that the air back flow is blocked out of the head housing.

The operation principle of the device in accordance with one embodiment of the invention will be described hereinbelow.

With reference to FIG. 4, when the drilling needle 3 is in operation, namely, when the powered wind wheel is rotating, the compressed air 21 for driving the powered wind wheel 7 escapes from the clearance of the bearing to blow the elastic rubber axle shroud 14, then the end face 16 at the center portion of the axle shroud is separated with the wind wheel axle 15, the air flow flows out from the circular clearance between the drilling needle 3 and the axle shroud 14, so that the drilling needle can be operated rotating normally. The bearing 6 can be cooled by the compressed air normally. Since the pressure compressed air flow inside of the head housing is positive, the fluid suckback phenomenon will not occur.

With reference to FIG. 5, when the drilling needle 3 stops rotating, the positive pressure compressed air 21 inside of the head housing will lose, and the center of the wind wheel axle 15 will form negative pressure due to inertia, which will result in the suckback phenomenon of the contaminated fluid. Owing to the elastic reaction of the elastic axle shroud, when the pressure in the turbine chamber decreases to a certain degree, the end face 16 of the axle shroud will contact the end face of the wind wheel axle 15 to generate hermetic seal and brake effect. At this point, there still has residual position pressure compressed air in the turbine chamber, thus the contaminated fluid cannot flow into the head housing. Besides, when the positive pressure in the head housing disappears and the negative pressure forms, the wind wheel axle is still rotating, the end face 16 of the axle shroud will press more tightly the end face of the wind wheel axle 15 at the atmospheric pressure so as to reinforce the effect of hermetic seal and brake.

When the dental drill handpiece starts rotating again, the turbine chamber will again be in a status of positive pressure, the axle shroud will be reblown out, the end face 16 of the axle shroud separates with the wind wheel axle 15, so that normal cutting and drilling operation can be started.

When the axle shroud is contacting the end face of the wind wheel axle, the rotation speed of the drilling needle will decrease largely, so that the abrasion to the rubber axle shroud is not serious, the requirement to the rubber material is not tough.

When the residual positive pressure in the turbine chamber still has not gone away, the drilling needle can be stopped operation, so that the suckback phenomenon of the contaminated fluid can be avoided completely.

The invention claimed is:

1. A suckback prevention device in combination with a single use high-speed turbine dental drill handpiece, said high-speed turbine dental drill handpiece comprising a drilling needle and a head comprising a head housing and a wind wheel axle, said wind wheel axle being disposed inside said head housing for driving the rotation of said drilling needle and said drilling needle being connected to said wind wheel axle, the suckback prevention device comprising
   an annular opening in a two-step profile shape;
   an elastic bowl-shaped axle shroud;
   an annular skeleton; and
   an annular screw;
wherein
   said annular opening is disposed in said head housing around said wind wheel axle and said drilling needle;
   said elastic bowl-shaped axle shroud and said annular skeleton are disposed in an inner-step part of said annular opening;
   an eyelet for said drilling needle is set at the center of said elastic bowl-shaped axle shroud, and the diameter of said eyelet is slightly larger than the outer diameter of said drilling needle;
   said elastic bowl-shaped axle shroud is disposed in said annular skeleton, and said elastic bowl-shaped axle shroud and said annular skeleton are hot pressed together; and
   said annular screw is disposed in an outer-step part of said annular opening for fixing said annular skeleton and said elastic bowl-shaped axle shroud.

2. The suckback prevention device of claim 1, wherein a center portion of said elastic bowl-shaped axle shroud is thicker than an annular strip between the center portion and the edge portion of said elastic bowl-shaped axle shroud.

3. The suckback prevention device of claim 1, wherein the material for said elastic bowl-shaped axle shroud is rubber or plastic.

4. The suckback prevention device of claim 1, wherein the material for said annular skeleton is metal or hard plastic.

5. A high-speed turbine dental drill handpiece, comprising:
   a drilling needle;
   a head comprising a head housing and a wind wheel axle; and
   a suckback prevention device comprising:
      an annular opening in a two-step profile shape;
      an elastic bowl-shaped axle shroud;
      an annular skeleton; and
      an annular screw;
   wherein
      said wind wheel axle is disposed inside said head housing for driving the rotation of said drilling needle;
      said drilling needle is connected to said wind wheel axle;
      said annular opening is disposed in said head housing around said wind wheel axle and said drilling needle;
      said elastic bowl-shaped axle shroud and said annular skeleton are disposed in an inner-step part of said annular opening;
      an eyelet for said drilling needle is set at the center of said elastic bowl-shaped axle shroud, and the diameter of said eyelet is slightly larger than the outer diameter of said drilling needle;
      said elastic bowl-shaped axle shroud disposed in said annular skeleton, and said elastic bowl-shaped axle shroud and said annular skeleton are hot pressed together; and
      said annular screw is disposed in outer-step part of said annular opening for fixing said annular skeleton and said elastic bowl-shaped axle shroud.

6. The high-speed turbine dental drill handpiece of claim 5, wherein a center portion of said elastic bowl-shaped axle shroud is relatively thick in comparison to an annular strip between the center portion and an edge portion of said elastic bowl-shaped axle shroud.

7. The high-speed turbine dental drill handpiece of claim 5, wherein the material for said elastic bowl-shaped axle shroud is rubber or plastic.

8. The high-speed turbine dental drill handpiece of claim 5, wherein the material for said annular skeleton is metal or hard plastic.

* * * * *